United States Patent [19]

Bowen

[11] 4,215,033
[45] Jul. 29, 1980

[54] COMPOSITE DENTAL MATERIAL

[75] Inventor: Rafael L. Bowen, Gaithersburg, Md.

[73] Assignee: American Dental Association Health Foundation, Washington, D.C.

[21] Appl. No.: 940,597

[22] Filed: Sep. 8, 1978

Related U.S. Application Data

[63] Continuation of Ser. No. 764,448, Jan. 31, 1977, abandoned.

[51] Int. Cl.$^2$ .................... A61K 5/06; C03C 15/00; C08K 3/40; C08L 33/12
[52] U.S. Cl. .................................... 260/42.15; 65/31; 106/35; 106/50; 106/54; 106/288 B; 106/299; 106/306; 260/998.11; 428/402; 433/222
[58] Field of Search .................... 260/42.15, 998.11; 106/35, 52, 54, 50, 40 V; 32/15; 65/31; 423/340; 428/402, 404

[56] References Cited

U.S. PATENT DOCUMENTS

| | | | |
|---|---|---|---|
| 2,306,021 | 12/1942 | Knowles et al. | 423/340 |
| 2,834,738 | 5/1958 | Vincent | 106/54 |
| 2,920,971 | 1/1960 | Stookey | 106/39.8 |
| 3,413,133 | 11/1968 | Stalego | 106/50 |
| 3,464,932 | 9/1969 | Connelly et al. | 106/52 |
| 3,630,700 | 12/1971 | Hammel | 65/31 X |
| 3,661,601 | 5/1972 | Dumbaugh et al. | 106/54 |
| 3,681,098 | 8/1972 | Dumbaugh et al. | 106/52 |
| 3,687,850 | 8/1972 | Gagin | 65/31 X |
| 3,728,139 | 4/1973 | Carrier et al. | 106/54 |
| 3,808,170 | 4/1974 | Rogers | 260/998.11 |
| 3,945,816 | 3/1976 | Johnson | 65/31 X |
| 3,971,753 | 7/1976 | Frechtling et al. | 428/404 |
| 3,971,754 | 7/1976 | Jurecic | 260/998.11 |
| 4,028,325 | 6/1977 | King et al. | 260/998.11 |
| 4,029,632 | 6/1977 | Gross | 260/998.11 X |
| 4,143,018 | 3/1979 | Crisp et al. | 260/998.11 |
| 4,157,907 | 6/1979 | Kroyer | 428/404 X |

FOREIGN PATENT DOCUMENTS 1963552 8/1970 Fed. Rep. of Germany ...... 260/998.11
992782 5/1965 United Kingdom .

OTHER PUBLICATIONS

Bowen, R. W. et al.—"A New Series of X-ray-Opaque Reinforcing Fillers for Composite Materials", J. Dental Research, vol. 51(1) 1972.
Wilson, A. D., "Alumino-Silicate Polyacrylic Acid and Related Cements"—Br. Polym. J., 1974, 6, pp. 165-179.
Bal'skaya, L. A. et al. "Phase Separation in Low-Alkali Bovosilicate Glasses Containing RO and $Al_2O_3$'-'—(1973) p. 107—The Structure of Glass vol. 8.
Grechanik, L. A. et al. "Properties of Glasses Exhibiting Phase Separation in the System, $SiO_2$—$B_2O_3$—$Al_2O_3$—ZnO—$Na_2O$ " (1973) p. 114—The Structure of Glass.
Milyukov, E. M. et al.—"Phase-Separation Phenomena in Glasses of Aluminosilicate Systems Containing Various Modifier Cations", pp. 158-161.
The Structure of Glass, vol. 8, (Ed. by Porai-Koshits) pub. by Consultants Bureau, N.Y. (1973).

Primary Examiner—Helen M. McCarthy
Attorney, Agent, or Firm—Allegretti, Newitt, Witcoff & McAndrews

[57] ABSTRACT

An improved composite dental material includes an inorganic component of glass particles separated into two interconnected vitreous phases which have been etched to produce a porous surface layer. The inorganic glass particles are combined with an organic resin to provide the composite dental material. Preferable glass compositions include a mixture of silicon dioxide, boron oxide, aluminum oxide and strontium oxide, with one or more from the group of calcium oxide, zinc oxide, stannic oxide, and zirconium oxide as optional modifying ingredients.

22 Claims, 2 Drawing Figures

COMPOSITE DENTAL MATERIAL

This is a continuation of application Ser. No. 764,448, filed Jan. 31, 1977, now abandoned.

BACKGROUND OF THE INVENTION

In a principal aspect, the present invention relates to an improved composite dental restorative material of the type including an inorganic glass component and an organic resin component.

Dental composite materials comprised of an inorganic component such as glass and an organic component such as a hardenable resin have been available since as early as 1965. Such materials are particularly valuable when used to restore the appearance and function of decayed, fractured, or otherwise defective or unsightly tooth surfaces. While prior art composite dental materials have proven to be adequate and beneficial for restoring teeth, they are often vulnerable to an undesirable amount of surface material loss under certain oral conditions. This has been referred to as loss of "anatomic form".

The reasons for loss of anatomic form have not been thoroughly established, though a hypothesis holds that there is a loss of surface filler particles due to inadequate or hydrolytically unstable adhesive bonding between the inorganic particle and the resin or polymer. This is then followed by wear of the polymer.

Individual filler particles are not worn away significantly when exposed on the surface since the bulk properties of most filler materials in use probably include adequate insolubility and resistance to wear. Thus, wear of filler particles is believed insignificant in comparison with the loss due to "plucking out" of weakly held particles because of forces resulting from a shearing of normal foods. A consequence of this hypothesis is that improved bonding between the filler materials and the organic polymeric matrix material is required.

The inventor previously disclosed a barium oxide-containing glass composition in "A New Series of X-Ray Opaque Reinforcing Fillers for Composite Materials", Journal of Dental Research, Volume 51, pages 177-182 (1972). The barium oxide composition disclosed in the referenced publication, however, produces a pH of about 9.3 when a 10% suspension of the composition is stirred in distilled water. This alkaline reaction may affect adversely the hydrolytic stability of the bonding between the organic polymer and the inorganic filler which results from the use of an organofunctional silane coupling agent interlayer.

To overcome such an adverse result and achieve other desirable features, continued experiments were conducted. Essential features of the filler for composite materials, where aesthetics of the composite restoration is important, include transparency and a refractive index in the vicinity of that of the composite resin polymer. This index of refraction is commonly about $n_D$ 1.55, although higher and lower values are sometimes encountered. Also, the inorganic filler component is preferably opaque to X-rays in order that subsequent evaluations and diagnostic studies, if necessary, may be performed by the dentist. The filler component should be nontoxic (except for certain industrial uses) and the thermal expansion coefficient should be minimized.

It was most fortunate that a kind of glass was discovered which, with proper preparation and treatment, seems capable of fulfilling all of the requirements of an inorganic component for a composite dental material comprised of the inorganic component and an organic resin or polymer component.

SUMMARY OF THE INVENTION

An improved inorganic, amorphous glass material in the form of two interconnected phases wherein one of the phases may be subjected to acid etching to selectively dissolve at least a portion of that phase, provides a semiporous filler particle for use in combination with an organic resin material. The result is an improved composite material for use in restorative or preventive dental practice. The inorganic glass material includes a combination of silicon dioxide, boron oxide, aluminum oxide and one or more compounds from the group consisting of strontium oxide, calcium oxide, zinc oxide, tin oxide, titanium oxide, niobium (columbium) oxide, zirconium oxide, tantalum oxide, and tungsten oxide. It may include barium oxide (BaO), lead oxide (PbO), bismuth oxide (Bi $O_n$), or other toxic oxides only if used exclusively for certain industrial applications that avoid risk to humans. Preferably, the composition is of silicon dioxide, boron oxide, aluminum oxide and at least one oxide selected from the group consisting of strontium oxide, calcium oxide and zinc oxide. Optionally, when the composition is intended for dental use, it may be modified up to about 25 mole percent by at least one oxide selected from the group consisting of zirconium oxide, tin oxide, titanium oxide, niobium oxide, tantalum oxide and tungsten oxide. The glass material is mixed in a conventional manner, quenched, pulverized and then heat treated to provide the interconnected two-phase morphology. Subsequent etching by acid, surface treatment with an organofunctional silane coupling agent, and mixing of the etched and treated semiporous filler particles of glass material with a liquid organic resin provide the composite dental material.

Thus, it is an object of the present invention to provide an improved inorganic glass for use in combination with organic resin to provide a composite dental filling material.

Another object of the present invention is to provide a method for manufacture of an improved inorganic amorphous two-phase glass for use in composite dental materials.

Still a further object of the present invention is to provide a semiporous inorganic filler particle useful in a composite dental material by providing increased interfacial area between inorganic and organic components of the composite as well as interpenetration and physical interlocking between the components.

A further object of the present invention is to provide an improved inorganic amorphous glass which is substantially transparent to visible light, opaque to X-rays, and nontoxic, with an index of refraction close to the refractive indexes of organic resins found in aesthetic composite dental restoration materials.

A further object of the developments described here is to provide a means by which spherical-shaped reinforcing filler particles can be caused to have a high surface area (interfacial area between reinforcing filler and dental resin).

These and other objects, advantages and features of the present invention will be set forth in the detailed description which follows.

BRIEF DESCRIPTION OF THE DRAWING

In the detailed description which follows, reference will be made to the drawing comprised of the following figures.

DESCRIPTION OF THE PREFERRED EMBODIMENT

Preliminary Concept

The concept considered is that a glass formulation, containing no monovalent elements, might be found which would have a suitable refractive index and, at the same time, would have a composition sufficiently near the center of a miscibility gap to form an interconnected phase morphology as a result of suitable heat treatment. Such a heat treated filler particle with two mutually penetrating phases then could be subjected to acid etching to dissolve selectively part of the more soluble phase. This would lead to interconnected porosity beginning at the surface of each reinforcing filler particle and extending to some optimal depth into the particle but not throughout the core of the particle. These "semiporous" filler particles could be treated then with the appropriate organofunctional silane coupling agent to obtain the specific chemical adhesion promoted by the silane with an organic resin.

Increased interfacial area, interpenetration and physical interlocking of the filler particle with the resin, in addition to the "chemical adhesion" mediated by a silane (or other) coupling agent, would be achieved. Since the refractive indexes of the two glass phases in such a composition would be different, phase separation would need to be controlled so that the dimensions of the two discrete (glass-in-glass) phases would not be large enough to scatter visible light appreciably.

Hood et al in U.S. Pat. No. 2,106,744 discloses a two-phase glass material having penetrating, distinct phases with one of the phases subject to acid etching. The compositions of Hood et al are not suitable for dental materials, however, because they do not have proper refractive indices, they are not radiopaque, and the solubilities of their low-silica phases are much too high for usefulness in the oral cavity.

It is noted that a porous or semiporous reinforcing filler in a wear-resistant dental filling material must have in addition to the desired refractive index, the condition of radiopacity; the opacity to X-rays is required so that subsequent radiographic diagnostic procedures can detect marginal defects, secondary caries and other conditions that might require remedial treatment.

Method of Preparation

Figure 1:
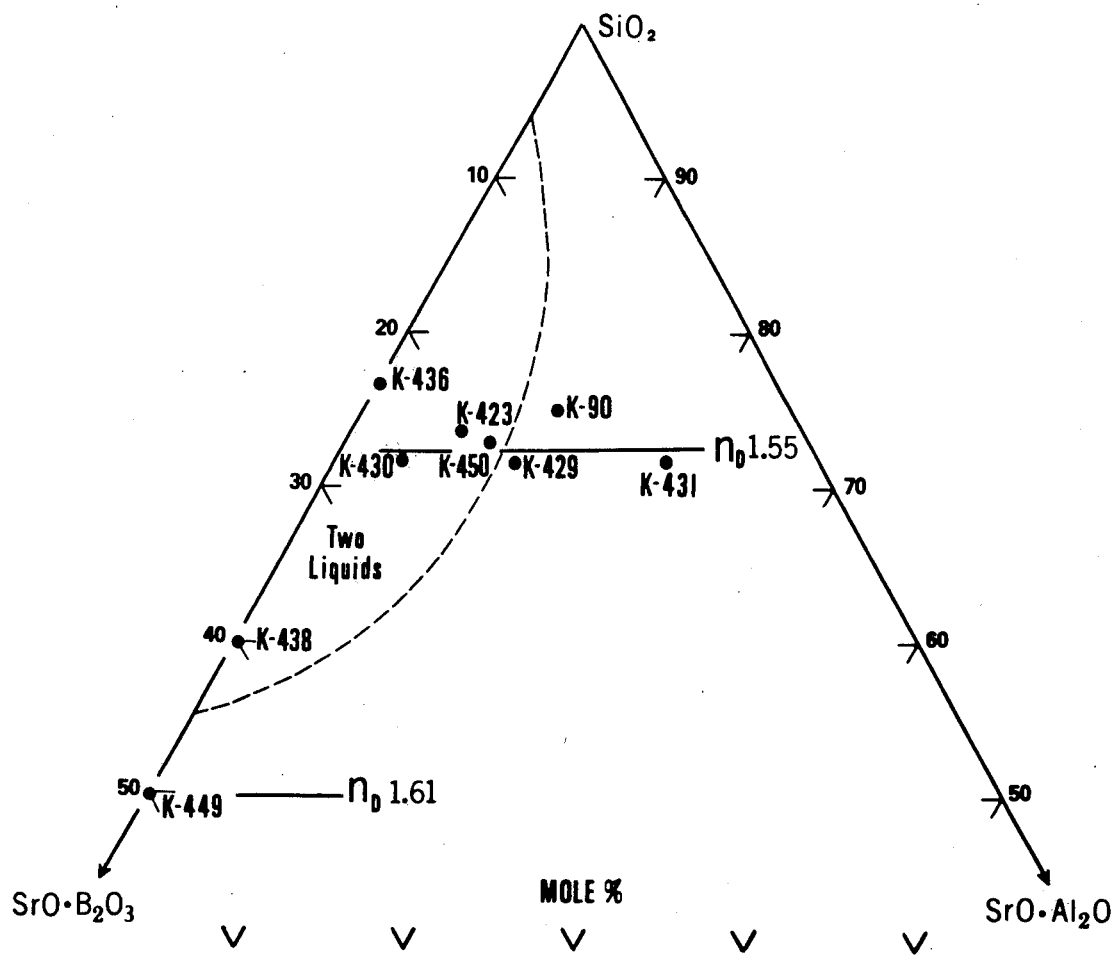
FIG. 1 is a ternary phase diagram for the system $SiO_2$—$SrO.B_2O_3SrO.Al_2O_3$ and identifies compositions given in Table 1 in which strontium oxide is the glass modifier.
Figure 2:
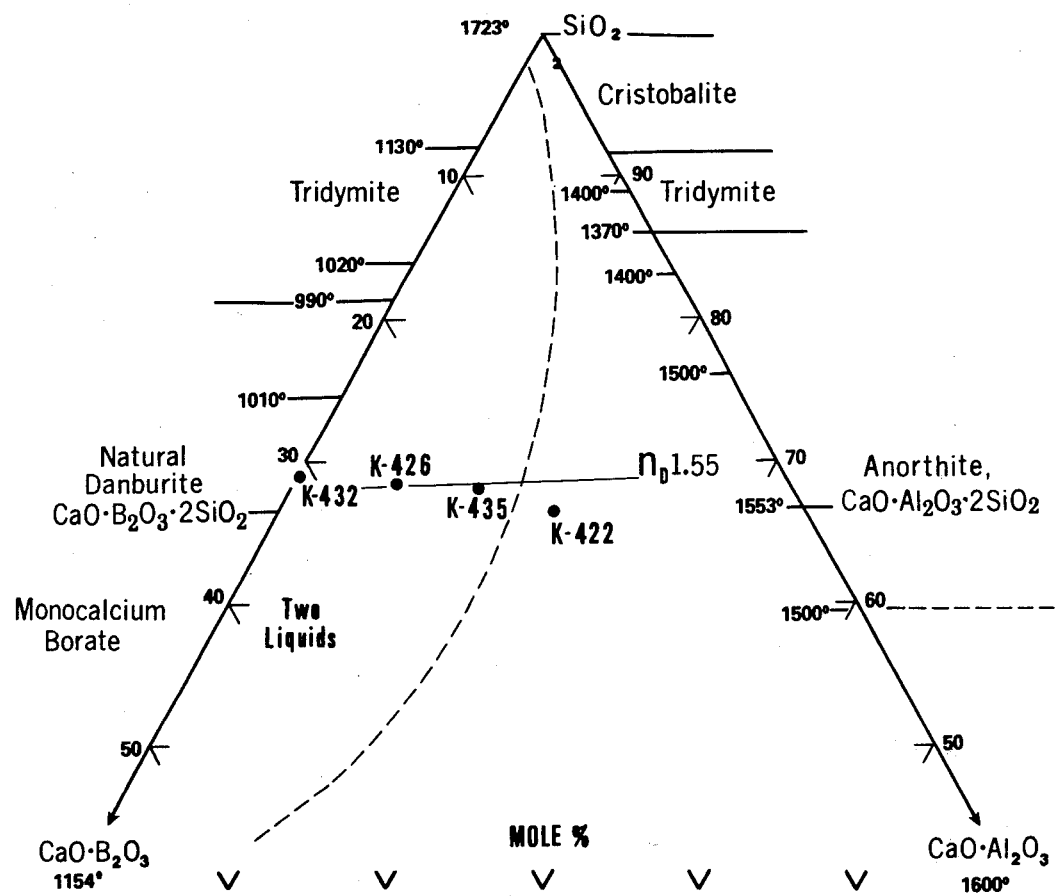
FIG. 2 is a ternary phase diagram for the system $SiO_2$—$CaO.B_2O_3$—$CaO.Al_2O_3$ and identifies compositions given in Table 1 in which calcium oxide is the glass modifier.

To identify satisfactory semiporous reinforcing glass components for dental composite materials, various compositions of glass were melted in an electric furnace in a platinum crucible 6.35 cm in diameter and 7.62 cm deep. Table I sets forth the compositions of each sample tested. FIGS. 1 and 2 illustrate the compositions on ternary diagrams.

The compositions within the curved broken line of FIG. 1 developed perceptible opalescence in the gradient furnace. The position of the upper end of the curved broken line was estimated by interpolation from immiscibility of compositions containing MgO, CaO, and BaO. Note that the subliquidus immiscibility boundary might extend somewhat farther in the direction of silica.

The compositions within the curved broken line of FIG. 2 developed perceptible opalescence in the gradient furnace. The positions of the upper and lower ends of the curved broken line (the boundaries of the two-liquids region along the line connecting $SiO_2$ and $CaO.B_2O_3$) are already known to those skilled in the art. The lower end (not shown) would be located at about 63 mole percent $CaO.B_2O_3$. The crystalline phases and estimated liquidus temperatures (in degrees C) are also known to those skilled in the art. The natural mineral danburite forms two liquids when melted, it does not recrystallize under ordinary conditions, and monocalcium borate ($CaO.B_2O_3$) forms below the liquidus temperature in this region.

TABLE 1

COMPOSITION AND PROPERTIES OF GLASSES IN WHICH MODIFIERS ARE EQUIMOLAR TO $B_2O_3$ PLUS $Al_2O_3$

| Glass No Record Ref. | Composition of Batch (mole %) | | | Modifiers | | | Description of Cast Portion | Water-Quenched Strings | Product | Refractive Index $n^2_D{}^5$ | Appearance in Microscope* |
|---|---|---|---|---|---|---|---|---|---|---|---|
| | $SiO_2$ | $B_2O_3$ | $Al_2O_3$ | SrO | CaO | ZnO | | | | | |
| 1 (K-431) | 56 | 7 | 15 | 22 | | | Clear, a few seeds | Clear | Clear | 1.552 | Minimal traces birefringent material |
| 2 (K-90) | 60 | 11 | 9 | 20 | | | Clear, small seeds | Clear | Clear | 1.545 | Practically no birefringent material |
| 3 (K-429) | 56 | 14 | 8 | 22 | | | Clear, faint trace of seeds | Clear | Clear | 1.551 | Faint trace of birefringence |
| 4 (K-450) | 57.4 | 14.9 | 6.4 | 21.3 | | | Clear, practically no seeds | Clear | Clear | 1.554 | Faint trace, if any birefringent material |
| 5 (K-423) | 58 | 16 | 5 | 21 | | | Opalescent, bluish by scattered; amber by transmitted light; no seeds | Clear | Clear | 1.546 | Very faint trace of birefringent inclusions |
| 6 (K-430) | 56 | 19 | 3 | 22 | | | Opaque, white glass, surfaces glossy to shiny | Opalescent | White to Clear | 1.550 | Faint trace of birefringent inclusions |
| 7 (K-436) | 62 | 19 | | | | 19 | (Quenched in crucible; seedy "sintered" | None | (Too viscous to pour) | 1.460 1.600 | Discontinuous phase; Continuous |

TABLE 1-continued

COMPOSITION AND PROPERTIES OF GLASSES IN WHICH MODIFIERS ARE EQUIMOLAR TO $B_2O_3$ PLUS $Al_2O_3$

| Glass No Record Ref. | Composition of Batch (mole %) | | | Modifiers | | | Description of Cast Portion | Strings | Water-Quenched Product | Refractive Index $n^2_D{}^5$ | Appearance in Microscope* |
|---|---|---|---|---|---|---|---|---|---|---|---|
| | $SiO_2$ | $B_2O_3$ | $Al_2O_3$ | SrO | CaO | ZnO | | | | | |
| | | | | | | | white masses) | | | | phase vitreous and birefringent material |
| 8 (K-438) | 42.8 | 28.6 | | 28.6 | | | Opaque white; surfaces glossy; no seeds visible | White | White | (1.579?) | Two liquid phase; practically no birefringence |
| 9 (K-449) | 33.4 | 33.3 | | 33.3 | | | Clear, no seeds; faint pink tint | None | Clear; Peach-colored | 1.606 | Traces of bifringent material |
| 10 (K-422) | 50 | 12 | 13 | | 25 | | Clear, practically no seeds | Clear | Clear | 1.556 | Practically no bifringence |
| 11 (K-435) | 51.4 | 15.2 | 9.1 | | 24.3 | | Clear, no seeds | Clear | Clear | 1.554 | Little, if any bifringent material |
| 12 (K-426) | 52 | 19 | 5 | | 24 | | Opaque, white glass; air surface dull fracture shiny | Clear to Opalescent | White to Clear | 1.548+ | Traces of birefringence |
| 13 (K-432) | 53 | 23.5 | | | 23.4 | | (Quenched in crucible; "sintered" masses) | None | (Could not pour) | 1.459 1.614 | Discontinuous; Continuous phase |
| 14 (K-451) | 55 | 5.4 | 17.1 | | | 22.5 | Clear, small seeds; surface glossy | Clear | Clear | 1.570 | Faint trace of bifringence |
| 15 (K-437) | 53.6 | 11.6 | 11.6 | | | 23.2 | Opalescent to White | Mostly Clear | Clear to Opalescent | 1.552+ (some to 1.566) | Trace of birefringent material |

*Crushed sample from small pieces of water-quenched product.
+Strain birefringence near phase interfaces.

After a batch was melted, it was stirred with a motor-driven platinum-10% rhodium double-bladed propeller-type stirrer to obtain homogeneity. The time of melting and firing depended on the characteristics of the melts as did the maximum temperature used. Usually about 1.5 hours were required to fill the crucible and melt the batch ingredients, and about the same length of time was required to stir the melt. The maximum temperature used in preparing the glasses was about 1,650° C.

When possible, a small amount of the molten glass was poured onto a metal surface and the rest was poured into clean water to quench the glass and break it into small pieces so that it could be ground conveniently. In most cases when the glasses were poured, the viscosity and flow characteristics resulted in the formation of air-quenched "strings" of glass, typically 1 to 2 mm in diameter. The refractive indexes were determined with a microscope by the oil-immersion method on small samples of water-quenched glass, which had been crushed in a steel mortar. Table 1 sets forth the observations of each test sample.

Subsequently, strings (if available) or small pieces of water-quenched glass were arranged in a continuous row in porcelain boats, and these were placed end to end in a vitreous silica tube and inserted into a horizontal tube furnace which had a thermal gradient. The temperatures in the gradient were recorded at each centimeter from 11 to 15 cm from the center of the furnace, the range in which tests disclosed opalescence occurred. After an isothermal heat treatment for 20 hours, the samples were air quenched. From these, a small portion of the glass (approximately 0.5 cm in length) which had been held at a temperature slightly lower than that which produced visible opalescence (the portion receiving the highest isothermal heat treatment that produced no visible opalescence) was removed and crushed with a steel mortar and pestle. The approximate temperature ranges to which these subsamples were held for twenty hours are given in Table 2.

TABLE 2

ETCHING CHARACTERISTICS OF MICROSCOPIC PARTICLES FROM HEAT-TREATED GLASS SAMPLES
Microscopic appearance of particles in phosphoric or hydrochloric acid solutions

| Glass No.[1]; Record Ref. | Heat Treatment Temperature Range[2] | 3N $H_3PO_4$ | | 3N HCl | |
|---|---|---|---|---|---|
| | | Time, Min[3] | Observations | Time, Min | Observations |
| 3 (K-429) | 740°–750° C. | 10 | No porous zones; no dissolution seen | 10 | No zones or dissolution seen |
| | | 30 | A few zones seen but not extending completely around peripheries | 30 | Some of the particles (~10%) had zones (typically 2 μm wide), most (~90%) did not. |
| | | | Overnight, some particles had wide zones (z 10 μm); these were stained when MB was added to slide; unstained particles had no zones, i.e. were not etched | 45 | MB stained parts and particles with zones; not those without |
| | | | | 240 | By 4 hours most, but not all of the remaining particles (and the remaining parts of particles) |

TABLE 2-continued
ETCHING CHARACTERISTICS OF MICROSCOPIC PARTICLES FROM HEAT-TREATED GLASS SAMPLES
Microscopic appearance of particles in phosphoric or hydrochloric acid solutions

| Glass No.[1]; Record Ref. | Heat Treatment Temperature Range[2] | 3N $H_3PO_4$ Time, Min[3] | Observations | 3N HCl Time, Min | Observations |
|---|---|---|---|---|---|
| | | | | | had developed zones (typically ~2 μm wide) but where not stained by MB [pores might be too fine to admit dye molecules] |
| 4 (K-450) | 740–750 | 4 | First evidence of porous zones | | |
| | | 10 | Zones typically ~1 μm wide (deep) | | |
| | | 30 | Zones typically 2 (1–10) μm wide | | |
| 5 (K-423) | 730–750 | 4 | First evidence of porous zones | | |
| | | 5 | Zones typically ~1 μm wide | | |
| | | 30 | Zones typically 4 (3–18) μm wide | | |
| 6 (K-430) | 700–730 | 3 | Outer edges less distinct, "zones" typically ~1 μm | 2 | Zones about 2μm wide |
| | | | | 5 | Zones about 4–8 μm wide |
| | | 10 | Some zones broke up spontaneously, yielding submicron particles which were slowly scattered by Brownian motion; one particle dissolved with no visible zone or Brownian particles | 10 | Smaller particles completely porous; larger had "cores" |
| | | 20 | Most particles had wide, tenuous "zones", about 50% dissolving or breaking up on some areas | 30 | No particles seen dissolving or breaking up |
| | | 40 | Stained by MB; leached and stained portions very fragile | | |
| 10 (K-422) | 740–770 | 8 | No zones visible | | |
| | | 13 | Possible zones (?) | | |
| | | 30 | All particles had rather uniform zones about 2 μm wide | | |
| | | 40 | Particles stained uniformly (flat, dark blue) with MB, halo effect[4] seen | | |
| 11 (K-435) | 760–790 | 6 | First evidence (appearance) of zones | | |
| | | 12 | Zones typically 1 μm wide | | |
| | | 30 | Typically 3 (2–10 μm) wide | | |
| | | 40 | Stained by MB | | |
| 12 (K-426) | 750–760 | 2 | Browian motion of submicron particulate material seen near edges of all particles (particles were slightly amber in transmitted light) | 2 | Brownian motion of submicron particulate material seen near edges of all particles (particles were slightly amber in transmitted light) |
| | | 30 | No zones; particles dissolving, some with a moth-eaten appearance; macro: milky appearance due to colloidal silica in suspension | 30 | No zones, particles dissolving, some with a moth-eaten appearance; macro: milky appearance due to colloidal silica in suspension |
| 12 (K-426) | 750–760 | 35 | MB Stained and "gelled" the colloidal suspension of silica (no Brownian motion); no general staining of the particles | 35 | Same as with the other acid, except that there was slightly more "integrity" of semi-connected silica residues |
| 14 (K-451) | 850–870 | 45 | Zones uncertain, if present | 15 | Possible zones ~1 μm wide |
| | | 90 | Zones typically 2 μm (1–4 μm) wide | 57 | MB stained immediately; zones ~1 μm wide |
| 15 (K-437) | 780–800 | 14 | Zones 1–2 μm wide | | |
| | | 24 | Zones typically 2 μm wide | | |
| | | 28 | Stained by MB | | |

[1] The chemical compositions of the glasses are given in Table 1 of reference 1, glass No. 5 in Table 2 of reference 2.
[2] Samples were selected from just below the temperature range which produced visible opalescence (in most compositions) after twenty hours in the gradient furnace; No. 16 and No. 15, after one hour in the gradient furnace.
[3] Time (minutes) in contact with etching solution, at room temperature.
[4] "Halo effect" refers to the depletion of dye (and blue color) from solution surrounding one or usually a cluster of stained particles. This effect (substantivity) was seen with most, if not all particles that promptly became dark blue in the blue solution.

Some crushed particles of each heated glass sample were then placed on a microscope slide. A drop of Since it would be expected that cationic dyes would have an affinity for the somewhat anionic surface of silica, and the etching out of one of the two interconnected glass phases (the dimensions of which are submicroscopic) would give a very large increase in accessible surface area, methylene blue solution was added to the slides after a period of etching with the acids (Table 2).

To obtain earlier feedback on the progress of etching and submicroscopic surface pore formation, a solution containing both phosphoric acid (3 N) and methylene blue (0.05%) was used (Table 3).

unetched particle; it had, however, a lower apparent refractive index.

Further description of the responses of the most promising compositions to etching by phosphoric or hydrochloric acid is given in Table 2. In cases where visible (microscopic) zones had developed in response to phosphoric acid solution, prompt, dark staining occurred when a methylene blue solution was added. However, particles that developed porous surface zones very slowly in 3 N HCl but not in 3 N $H_3PO_4$ solutions did not generally become perceptibly stained in methylene blue solutions (after etching). Particles that did not

TABLE 3

ETCHING AND STAINING CHARACTERISTICS OF MICROSCOPIC
PARTICLES FROM HEAT-TREATED GLASS SAMPLES
Etching and Staining in an Acidic Dye Solution
(3N $H_3PO_4$ Plus 0.05% Methylene Blue)

| Glass No.; Record Ref. | Heat Treatment Temperature Range | Time, Min[1] | Microscopic Appearance |
|---|---|---|---|
| 3 (K-429) | 740°–750° C. | 2.2 | There was no evidence of staining of most of the particles; some partially; a few were completely stained. |
| | | 17.5 | Some previously unstained now stained slightly, one entirely deep blue, a few half-clear and half-stained, most remained unstained. Most remained unstained at 22 hours. |
| 4 (K-450) | 740–750 | 2.1 | With additional time, the particles stained uniformly to a flat, dark blue. |
| 4A (K-450) | 700 | 2.5 | Some (~60%) stained; a few very dark; by 3.4, all were uniformly stained medium - dark blue. |
| 5 (K-423) | 730–750 | 1.8 | By 3.9, all were uniformly stained dark, flat blue. |
| 5A (K-423) | 700 | 2.1 | By 2.8, ~90% were stained medium blue. |
| 6 (K-430) | 700–730 | 2.9 | ~50% of particles lightly stained. At 10 min, some remained unstained while others became dark. At 12 min, some were dissolving. |
| 10 (K-422) | 740–770 | 2.8 | By 8 min, all were uniformly stained dark blue. |
| 11 (K-435) | 760–790 | 2.4 | By 6 min, all were uniformly stained dark blue. |
| 12 (K-426) | 750–760 | — | By 75 min, no evidence of staining; particles dissolving. At 105 min, particles disappearing; very fine (< 1 μm) colloidal material stained as separated, insoluble fragments. By 130 min, most particles completely gone. |
| 14 (K-451) | 850–870 | 6.5 | Particles very lightly stained. At 15 min, all were uniformly pale blue. At 25 min, all were uniformly medium blue. |
| 15 (K-437) | 780–800 | 4.6 | ~50% lightly stained. By 8 min, all were stained. |

[1]Time (Minutes) at which particles first appeared unequivocally a darker blue compared with the background solution, at room temperature.

Some of the glass formulations, for example, Nos. 4, 5, 10 and 11, have the desired refractive indexes (near $n_D1.55$) and, at the same time, have compositions sufficiently near the centers of miscibility gaps so as to form interconnected phase morphologies of submicroscopic dimensions as a result of a suitable heat treatment.

The refractive indexes for phases of the glass formulations to be employed as a dental filler material should fall between 1.45 and 1.75, and the overall apparent refractive index is preferably between 1.5 and 1.6.

When particles of these heat-treated glasses were exposed to aqueous acid solutions under a cover glass, porous zones could be seen developing and growing inward from the edges of the glass particles with the aid of an optical microscope. The widths (depths) of the porous zones, as described in Table 2, should not be compared quantitatively since the apparent width is a function of the surface angle and orientation of irregular particles when viewed in the optical microscope.

When these particles were subjected to the acid solution for a prolonged period, the zones of interconnected porosity slowly progressed centrally until the "core" finally disappeared completely. This left what appeared to be a particle of the same size and shape as the original form zones in response to prolonged exposure to either acid did not become stained.

When the particles of certain heat-treated compositions were exposed to an aqueous solution that contained both phosphoric acid and methylene blue, simultaneous etching and staining occurred, with the particles becoming dark blue before the depth of the porosity had become sufficient to see (with the binocular optical microscope) as a zone around the particles. This combined etching and staining technique made it possible to identify candidate semiporous glass filler materials wherein the pore size and depth of the porous region are both too small to be detected directly by optical or scanning electron microscopic methods. The results of this etching and staining technique are given in Table 3. In general, it has been found that the preferred depth of acid etch for the glass component is in the range of 10 to 10,000 angstroms with the most preferred range being 250 to 300 angstroms.

There is a possible problem that might develop in the oral cavity wherein the reinforcing filler particles are exposed to the oral environment at the surface of dental restorations which have been contoured to reproduce the desired shape of the tooth. This surface layer of particles is faceted as a result of finishing and polishing operations by the dentist. Additive oxides have been sought which would partition into the more-soluble phase of the two component glass, and which would render this phase less soluble in the acids which frequent the oral cavity. This is to avert a problem that might arise if the soluble phase is slowly but continually etched or leached out of these surface particles by action of oral acids and chelating agents (for example citric acid); the high ("internal") surface area of the leached glass might then adsorb pigments or other staining materials which are also found in the oral cavity on occasion, and thereby might develop a degree of discoloration which would be undesirable. It was discovered that the addition of stannic oxide reduces the acid solubility of the low-silica phase. Stannic oxide apparently partitions into the low-silica phase (during the preparation) and (thereafter) reduces acid solubility.

There is also a conceivable problem wherein the akalinity of the more-soluble phase (to the extent that it contains relatively electropositive elements such as akaline earths) might cause or promote autolysis of this phase or some dissolving of the high-silica phase, or both. Therefore, alkaline-insoluble components have been sought. It was discovered also that zirconium oxide partitions into the low-silica phase and reduces its solubility in water or in alkaline solutions.

By the addition of stannic oxide, the compositions can be made more resistant to etching or leaching. The use of stronger acids is necessary in the preparation step which forms the shallow surface pores, but this is quite feasible in manufacturing processes. The relatively weak acids which are repeatedly present in the oral cavity cannot then produce the undesired leaching or etching of surface particles. The addition of zirconium oxide reduces the solubility of the low-silica phase in water and alkaline solutions. The use of these together thereby increases, synergistically, the color stability potential and chemical durability of the final product.

The most-preferred embodiment of the invention may use both stannic and zirconium oxides to simultaneously increase resistance to unwanted etching or leaching by the relatively weak acids and alkaline substances that frequent the oral environment.

Discussion

The nature of subliquidus liquid-liquid phase separation is such that the dimensions of the two phases depend primarily upon the thermal history: lower temperatures and shorter times at a given temperature tend to give smaller dimensions. As time or temperature is increased, the dimensions of the separated phases become progressively coarser. In some cases, excessive heating has been observed to coarsen interconnected phases of submicroscopic dimensions into dispersed droplets of (larger) microscopic dimensions.

The refractive indexes of the two phases are quite different. One phase is predominantly silica, with a refractive index of approximately $n_D = 1.459$. The other phase, containing mostly the other ingredients and a smaller amount of silica, which amount is determined by its solubility in these ingredients at a given temperature, has a higher refractive index. Consequently, if the dimensions of the phases are coarse enough, the material will scatter light and appear opalescent or opaque, especially if the phase dimensions are comparable to the wavelength of visible light. However, if the dimensions of the phases are fine enough, the material will be transparent, which is preferable for the intended application. It is for these reasons that most of the samples in this study were taken from just below the temperature range which produced visible opalescence in the gradient furnace during a convenient time of heat treatment.

Composition No. 4 (57.4 $SiO_2$, 14.9 $B_2O_3$, 6.4 $Al_2O_3$, and 21.3 SrO in mole percent, and 47 $SiO_2$, 14 $B_2O_3$, 9 $Al_2O_3$, and 30 SrO in weight percent) is one of the preferred glass compositions. It forms a clear, colorless glass with ordinary glass-making procedures, does not have ingredients as toxic as barium oxide and yet has X-ray opacifying characteristics due to the strontium oxide content. It has a refractive index ($n_D$ 1.55) suitably close to those of polymers used in dental composites, can be phase separated by a simple isothermal heat treatment to form interconnected phase morphology and can be subsequently ground and etched to form semiporous filler particles for reinforcing experimental composite resins.

Composition No. 5 (Table 1), another preferred glass composition, is similar to No. 4, except that it phase separates and becomes opalescent more readily. In fact, some of the clear, quenched glass, without heat treatment, developed etch zones when subjected to hydrochloric acid solutions. They did not, however, form these in phosphoric acid solution nor did they given uniform staining with methylene blue. Presumably, the phase separations were "nascent" and of extremely fine dimensions.

Composition No. 16 (record reference K-540; not shown in the tables) is one of the most preferred compositions; it contains: $SiO_2$ (silicon oxide) 58 mole percent, $B_2O_3$ (boron oxide) 15 mole percent, $Al_2O_3$ (aluminum oxide) 6 mole percent, and SrO (strontium oxide) 21 mole percent, which is about 48% silicon oxide, 14% boron oxide, 8% aluminum oxide and 30% strontium oxide by weight. Its composition and properties are intermediate between those glasses No. 4 and 5.

The heat-treated No. 6 composition (Table 1) had some interconnectivity of the silica phase (Table 2, HCl etch). The breaking up of the zones, in about 50% of the particles, when phosphoric acid was used suggested that much of the silica was in the form of droplets dispersed in the continuous soluble phase, with only a small degree of interconnectivity of the silica phase. The hydrochloric acid seems to attack the tenuous silica less than does the phosphoric acid.

Composition No. 10 which formed a clear glass that did not develop visible opalescence in the gradient furnace during 1, 2 or 20 hours did, nonetheless, undergo phase separation into two interconnected phases of submicroscopic dimensions, as disclosed by its etching and staining characteristics, when heating between 740° C. and 770° C. for 20 hours (Tables 2 and 3).

Within the compositions having calcium oxide as the modifier, No. 11 is the composition with the preferred characteristics. It can be formed and cast into clear glass, and heat treated to develop interconnected phase morphology with phase dimensions either submicroscopic or larger (opalescent). While this composition is not adequately radiopaque, it is useful as a dental filler component in that it may form the basis for more complex compositions containing X-ray opaque elements, especially those which will decrease the solubility of the low-silica phase.

Composition No. 12, with less $Al_2O_3$ than No. 11, tended to separate into phases more readily. In the heat-treated sample, the insoluble high-silica phase had the form of discrete colloidal droplets, dispersed in a continuous, acid-soluble, low-silica phase. In this composition, as in No. 6, this lack of interconnectivity developed by a "coarsening" during the heat treatment, since the clear, quenched, unheated samples of No. 12 and No. 6, when etched with either acid, promptly developed intact zones and stained dark blue when methylene blue was present.

Both compositions containing zinc oxide, No. 14 and No. 15, evidently formed two interconnected phases when quenched and then heat treated. The rates at which the soluble phases dissolved in the strong acids were slower than those of many of the other compositions.

In certain industrial applications, toxicity and resistance to chemical attack are of no concern. This might be the case in structural materials where strength, cost, certain optical properties and X-ray opacity are important. In such a situation, a two-phase, vitreous inorganic material of the present invention might be desirable, especially if it contained up to as high as 50 mole % of at least one additional ingredient selected from a group consisting of barium oxide (BaO), lead oxide (PbO), and bismuth oxide ($Bi_2O_3$) in addition to (or substituted for) the aforementioned oxide materials.

Although the compositions described here (Table I) have compositions in which the modifiers (SrO, CaO, etc.) are equimolar to $B_2O_3$ plus $Al_2O_3$, the scope of the invention includes compositions in which these modifiers are not equimolar to $B_2O_3$ plus $Al_2O_3$. The phase separations leading to the interconnected, interpenetrating vitreous phases do not require that the modifiers be equimolar to the $B_2O_3$ plus $Al_2O_3$. The reason they are so in these examples is that when these proportions hold, advantage is taken of the so-called "aluminoborate anomaly". It is fairly well-known in the glass-making art that in compositions in which elements that are sufficiently low in electronegativity are in certain proportions to the boric oxide, the boron takes on a 4-coordinated, tetrahedral, stereochemical configuration. Similarly, the aluminum ion likewise takes on 4-fold coordination and tetrahedral configuration in the presence of elements with sufficiently-low electronegativity. The transformation of these oxides into tetrahedral configuration is accompanied by a lowering of the coefficient of thermal expansion (and certain other, mostly-favorable changes) of the glasses containing them.

While it is believed that the dental material would benefit from the use of proportions leading to the formation of maximal 4-coordinated boron and aluminum ions, most of the desirable features of the present invention do not require this. However, it is preferred to have this particular stoichiometry in order to obtain and enjoy the lowest possible coefficient of thermal expansion; the hard tooth tissues have coefficients of thermal expansion that are lower than the composite materials of the present state of the art. Therefore, it is a preferred embodiment to obtain the minimal possible coefficient of thermal expansion in the filler and in the composite material.

A homogeneous glass material characterized by the aluminoborate anomaly, while lacking the porous surface which provides some of the significant advantages to the present invention, may nonetheless find use as a filler, flake or fiber in dental, medical or industrial resin composites. A preferred composition for such use would be a homogeneous, single-phase vitreous mixture of 34 to 80 mole % silicon oxide ($SiO_2$), 7 to 30 mole % boron oxide ($B_2O_3$), 3 to 17 mole % aluminum oxide ($Al_2O_3$), and 10 to 33 mole % of at least one modifier from a group consisting of strontium oxide (SrO), calcium oxide (CaO) and zinc oxide (ZnO), with the molar sum of the modifiers being substantially equimolar to the boron oxide plus the aluminum oxide, and the refractive index lying within the range of $n_D$ 1.49 to 1.61.

Notable by their absence are monovalent elements such as sodium ($Na_2O$), potassium ($K_2O$), lithium ($Li_2O$), etc. However, the present invention does not preclude the use of small amounts of these substances, but their use or incorporation is considered undesirable, because, in most instances, they would lower the chemical resistance (sometimes called "weather resistance") of the glass and probably would lower the durability of the dental composite material.

It is also known by many of those skilled in the art that spherical particles will pack together more closely than will particles of irregular shape having approximately the same size. Furthermore, an intermittent size distribution (that is, two or more different sizes with intermediate sizes omitted, sometimes called "gap grading") of spherical particles will, under random packing conditions, fit together even more closely, requiring less interstitial resin material. There are a number of benefits which arise from minimizing the resin content; these include less hardening shrinkage, a lower overall coefficient of thermal expansion, higher modulus of the elasticity (stiffness), and other beneficial characteristics.

It is expected that spherical particles of the semiporous reinforcing filler materials of the present invention, can be prepared by passing crushed, irregular particles (before or after size segregation) through an oxyacetylene flame, a plasma device, or other means of heating particles to an appropriate temperature, after which their temperature is quenched rapidly so that they retain the spherical shape on collection, provided that the temperatures of the particles do not rise so high as to allow appreciable or significant loss of individual ingredients by volatilization. The spherical, quenched, homogeneous glass particles may then (with or without alteration of size distribution at this stage), optionally be heat treated so as to form the two interpenetrating vitreous phases within the spherical particles; subsequent surface etching and silane treatment can then prepare the particles for use as reinforcing fillers (with or without further alteration of the size distribution).

Spheroidization of filler particles for use in dental composites is not currently practiced. This is due in part to the opinion of some, which holds that decreasing the interfacial area between filler and resin may degrade certain physical properties. Whether or not this is correct, the present invention provides means for answering these objections by greatly increasing the surface area (and the interfacial area between resin and filler) of the spherical filler particles.

Within certain limitations, the present invention can be applied also to other reinforcing filler morphologies, such as for example flakes, fibers, rods, or large inserts. In general, the preferred range of spherical particles is less than 5.0 millimeters diameter. Of course, the particles may not be perfectly spherical, but may assume a desired shape having a major dimension less than 5.0 millimeters. Flakes preferably have a thickness less than 100 μm (micrometers) and fibers preferably have a diameter less than 75 μm (micrometers).

Conclusions

As can be understood from a study of FIGS. 1 and 2 and the descriptions of the compositions given as examples, it is impossible to give exact compositional ranges circumscribing the invention. This is due in part to the shape of the immiscibility region which would require a third dimension to define its complex surface shape.

However, from the figures can be seen, generally, the nature of the immiscible region; alternatively, regions within which stable, single-phase glasses can be formulated and prepared can also be deduced by one reasonably skilled in the glassmaking art. Compositions (more or less) within the regions marked "two liquids" tend to separate into two phases upon heating; those reasonably near the "verticle" center of this region tend to form interconnected, interpenetrating phases as a result of heating. Those toward the left tend to separate prematurely or do not form homogeneous melts. Proceeding toward the right, those near the dotted line, (for example K-450 or K-435) are the most preferred since they can be easily melted, quenched, and caused to phase separate in a controlled manner. Continuing further toward the right (beyond the dotted line) are compositions yielding relatively stable, single-phase clear glasses with generally good physical properties. To the extreme right, however, glasses are increasingly viscous and less stable against devitrification. Within reasonable limits, compositions with higher silica content can be prepared having lower refractive indexes, and compositions with lower silica contents can be prepared having higher refractive indexes. Experimentation may be performed to set precise boundaries for compositions with very high or very low silica ($SiO_2$), boric oxide ($B_2O_3$), or alumina ($Al_2O_3$) concentrations, however.

It can be concluded by a perusal of the tables and the Figures, that the compositional ranges are probably as wide as the following: $SiO_2$ 33 to 80 mole %, $B_2O_3$ 7 to 33 mole %, $Al_2O_3$ 1 to 17 mole %, and CaO 5 to 25 mole %, or SrO 3 to 33 mole %, or a combination of CaO plus SrO plus ZnO about 3 to 33 mole %.

Following are the preferred compositions (in mole %):

A. 51.4 $SiO_2$, 15.2 $B_2O_3$, 9.1 $Al_2O_3$, 24.3 CaO;
B. 58 $SiO_2$, 15 $B_2O_3$, 6 $Al_2O_3$, 21 SrO;
C. 64.4 $SiO_2$, 17.8 SrO, 4.4 $Al_2O_3$, 8.4 $B_2O_3$, 5.0 $SnO_2$; and
D. 68.8 $SiO_2$, 13.1 SrO, 9.4 $B_2O_3$, 3.7 $Al_2O_3$, 5.0 $ZrO_2$.

The preferred method of manufacture of useful inorganic fillers includes melting, mixing, and homogenizing the constituents, quenching the melt, heat treating the composition to obtain separation into two interconnected vitreous phases, cooling, crushing the material to the desired particle sizes, etching away part of one phase, treating the irregular surfaces with an organofunctional silane coupling agent, and mixing the inorganic filler with an organic material.

Thus, while there has been set forth a preferred embodiment of the invention, the invention should be limited only by the following claims and their equivalents.

What is claimed is:

1. In a dental resin composite comprising a resin and a nontoxic filler, the improvement which comprises employment of a filler comprising a substantially transparent inorganic glass material which is a two-phase vitreous mixture of silicon dioxide ($SiO_2$), boron oxide ($B_2O_3$), aluminum oxide ($Al_2O_3$) and at least one oxide selected from the group consisting of strontium oxide (SrO), calcium oxide (CaO) and zinc oxide (ZnO), and which is substantially free of monovalent elements, wherein the refractive indexes of the phases are within the range of 1.45 to 1.75; wherein the morphologies of the phases are two continuous, interpenetrating networks of submicroscopic dimension which interlock and twist one phase through the other; and wherein one of the phases is partially removed at the surface to define pores.

2. The material of claim 1 wherein the range of depth of the pores is about 10 to 10,000 angstroms.

3. The material of claim 1 wherein the depth of the pores is in the range of 250 to 300 angstroms.

4. The material of claim 1 wherein said material comprises generally spherical particles with a diameter of less than 5.0 millimeters.

5. The material of claim 1 wherein said material comprises flakes of generally less than 100μ meters in thickness.

6. The material of claim 1 wherein said material comprises fibers of generally less than 75 μm in diameter.

7. The material of claim 1 wherein the overall apparent refractive index is within the range of $n_D$ 1.5 to 1.6.

8. The material of claim 1 wherein said mixture includes strontium oxide from said group and wherein said mixture is substantially radiopaque.

9. The material of claim 1 wherein the surface of the material is treated with an organofunctional silane adhesion promoting coupling agent whereby a chemical adhesion mechanism and a bonding mechanism involving physical penetration and interlocking contribute to the improved integrity and durability of the glass material in combination with an organic resin.

10. The material of claim 1 in combination with a polymerizable liquid organic resin to form a composite material.

11. The material of claim 1 wherein the components of the two phase glass material are modified up to about 25 mole % by at least one oxide selected from the group consisting of zirconium oxide, tin oxide, titanium oxide, niobium oxide, tantalum oxide and tungsten oxide.

12. The material of claim 1 wherein said material comprises about 48 weight % silicon dioxide, about 14 weight % boron oxide, about 8 weight % aluminum oxide and about 30 weight % strontium oxide.

13. The material of claim 1 wherein said material comprises about 48 weight % silicon dioxide, about 16 weight % boron oxide, about 15 weight % aluminum oxide and about 20 weight % calcium oxide.

14. The material of claim 1 wherein said material comprises a mixture of about 46 weight % silicon dioxide, about 5 weight % boron oxide, about 24 weight % aluminum oxide and about 25 weight % zinc oxide.

15. The material of claim 1, wherein the boron oxide ($B_2O_3$) plus aluminum oxide ($Al_2O_3$) are equimolar to strontium oxide (SrO) plus calcium oxide (CaO).

16. The material of claim 1 wherein said material comprises a mixture of about 33 to 80 mole % silicon dioxide, 7 to 33 mole % boron oxide, 1 to 17 mole % aluminum oxide and either 3 to 33 mole % strontium oxide or 5 to 25 mole % calcium oxide or 3 to 33 mole % of a combination of strontium oxide, calcium oxide and zinc oxide.

17. The material of claim 2, 3 or 7 wherein said material contains 3 to 33 mole % strontium oxide.

18. The material of claim 17 wherein said material contains no monovalent elements.

19. Substantially transparent glass particles less than 5.0 millimeters in diameter consisting essentially of 51.4 mole % silicon oxide ($SiO_2$), 15.2 mole % boron oxide ($B_2O_3$), 9.1 mole % aluminum oxide ($Al_2O_3$) and 24.3 mole % calcium oxide (CaO), said particles having as a morphology a two phase interpenetrating, twisting and interlocking network of submicroscopic dimension, with the low silica phase etched to a depth of less than 10,000 Angstroms, and suitable for use in a dental composite.

20. Substantially transparent glass particles less than 5.0 millimeters in diameter consisting essentially of 58 mole % silicon oxide ($SiO_2$), 15 mole % boron oxide ($B_2O_3$), 6 mole % aluminum oxide ($Al_2O_3$) and 21 mole % strontium oxide (SrO), said particles having as a morphology a two phase interpenetrating, twisting and interlocking network of submicroscopic dimension, with the low silica phase etched to a depth of less than 10,000 Angstroms, and suitable for use in a dental composite.

21. Substantially transparent glass particles less than 5.0 millimeters in diameter consisting essentially of 64.4 mole % silicon oxide ($SiO_2$), 17.8 mole % strontium oxide (SrO), 4.4 mole % aluminum oxide ($Al_2O_3$), 8.4 mole % boron oxide ($B_2O_3$), and 5 mole % tin oxide ($SnO_2$), said particles having as a morphology a two phase interpenetrating, twisting and interlocking network of submicroscopic dimension, with the low silica phase etched to a depth of less than 10,000 Angstroms, and suitable for use in a dental composite.

22. Substantially transparent glass particles less than 5.0 millimeters in diameter consisting essentially of 68.8 mole % silicon oxide ($SiO_2$), 13.1 mole % strontium oxide (SrO), 9.4 mole % boron oxide ($B_2O_3$), 3.7 mole % aluminum oxide ($Al_2O_3$), and 5 mole % zirconium oxide ($ZrO_2$), said particles having as a morphology a two phase interpenetrating, twisting and interlocking network of submicroscopic dimension, with the low silica phase etched to a depth of less than 10,000 Angstroms, and suitable for use in a dental composite.

* * * * *

UNITED STATES PATENT AND TRADEMARK OFFICE
CERTIFICATE OF CORRECTION

PATENT NO. : 4,215,033

DATED : July 29, 1980

INVENTOR(S) : Rafael L. Bowen

It is certified that error appears in the above—identified patent and that said Letters Patent is hereby corrected as shown below:

Title page, col. 2, at OTHER PUBLICATIONS, "Bowen, R.W." should be --Bowen, R. L.--; "Bovosilicate" should be --Borosilicate--; and "$Al_2O_3$'-'-" should be --$Al_2O_3$"--.

Col. 2, line 57, "X-rays," should be X rays,--.

Col. 4, line 12 "X-rays" should be --X rays--.

Table 1, heading in cols. 4 and 6, "Refractive Index $n^{25}_D$" should be --Refractive Index $n_D$ --, and col. 3, last line, "7(K-436) 62 19    19" should be --7(K-436) $62^D19$   19--.

Table 2, under the Observations col., the line "had wide zones (z 10μm)" should be --had wide zones (10 μm)--; Table 2-continued under the Observations col., line "breaking up on some areas" should be --breaking up in some areas--; and line "Browian motion of submicron" should be --Brownian motion of submicron-- Table 2, line "12(K-426) 750-760 35" delete --12(K-426) 750-760--. Table 2, footnote 1, after "Table 1" delete end of sentence.

Col. 7, last 2 lines, after "A drop of" remainder of paragraph was omitted, add --aqueous acid was added and covered with a microscope cover glass. In preliminary explorations, various concentrations of hydrochloric acid were used; three normal hydrochloric acid (3 molar; about 10.4%) was selected because of its proven effectiveness with other glass compositions. However, the volatility of this acid was undesirable and three normal phosphoric acid (one molar; about 9.3%) was considered preferable for observations with the binocular microscope. The widths of the porous zones in μm(micrometers, microns) were estimated with the aid of calibrated filar microscope eyepiece. A stopwatch was used to determine the time required for the response to these solutions.--

UNITED STATES PATENT AND TRADEMARK OFFICE
CERTIFICATE OF CORRECTION

PATENT NO. : 4,215,033
DATED : July 29, 1980
INVENTOR(S) : Rafael L. Bowen

It is certified that error appears in the above—identified patent and that said Letters Patent is hereby corrected as shown below:

Col. 9, line 47 "$n_D1.55$" should be --$n_D$ 1.55--.

Col. 12, line 26, "given" should be --give--.

Col. 16, line 58, "3to" should be --3 to--.

Signed and Sealed this

Second Day of November 1982

[SEAL]

Attest:

GERALD J. MOSSINGHOFF

Attesting Officer    Commissioner of Patents and Trademarks